United States Patent [19]

Panjwani

[11] Patent Number: 6,037,333
[45] Date of Patent: Mar. 14, 2000

[54] MICROBE-INHIBITING COMPOSITIONS

[75] Inventor: Noorjahan A. Panjwani, Medford, Mass.

[73] Assignee: Trustees of Tufts College, Boston, Mass.

[21] Appl. No.: 09/074,266

[22] Filed: May 7, 1998

[51] Int. Cl.[7] .................................................. A61K 31/70
[52] U.S. Cl. .............................................. 514/62; 514/25
[58] Field of Search ........................................ 514/25, 62

[56] References Cited

U.S. PATENT DOCUMENTS

| | | | |
|---|---|---|---|
| 4,640,912 | 2/1987 | Hausman | 514/54 |
| 4,701,444 | 10/1987 | Segal et al. | 514/55 |
| 4,971,956 | 11/1990 | Suzuki et al. | 514/55 |
| 5,141,925 | 8/1992 | Alroy et al. | 514/23 |
| 5,288,488 | 2/1994 | Backman et al. | 424/93 D |
| 5,455,240 | 10/1995 | Tuamanen et al. | 514/210 |
| 5,584,877 | 12/1996 | Miyake et al. | 623/1 |

FOREIGN PATENT DOCUMENTS

| | | |
|---|---|---|
| 0 057 323 A2 | 8/1982 | European Pat. Off. . |
| 95/33467 | 12/1995 | WIPO . |
| WO 95/34678 | 12/1995 | WIPO . |
| WO 96/30026 | 10/1996 | WIPO . |

OTHER PUBLICATIONS

Morton et al. *Infection and Immunity* Oct. 1991, 59(10), 3819–3822.

Marcus et al. *Infection and Immunity* Apr. 1989, 57(4), 1050–1053.

Merkel et al. *FEMS Immunology and Medical Microbiology* 1997, 19, 203–213, month not available.

Cao, Z. et al., "α–Man and Man(α1–3)Man Units are Potent Inhibitors of Acanthamoeba–Induced Cytopathic Effect," ARVO Annual Meeting, Fort Lauderdale, Florida, May 10–15, 1998, Abstract Book in *Investigative Opthalmology & Visual Science* 39(4):S147, abstract No. 686–B609, Mar. 1998.

Cao, Z. et al., "Mannose–Specific Inhibition of Acanthamoeba–Induced Cytopathic Effect," 20th Biennial Cornea Research Conference, Boston, Massachusetts, Abstract Book, p. 54, Sep. 25–27, 1997.

Panjwani, N. et al., "Mannose–Mediated Adhesion of Acanthamoeba to Corneal Epithelium Induces Expression of a Metalloproteinase," ARVO Annual Meeting, Fort Lauderdale, Florida, May 10–15, 1998, Abstract Book in *Investigative Opthalmology & Visual Science* 39(4):S147, abstract No. 687–B610, Mar. 1998.

Panjwani, N. et al., "Mannose–Specific Inhibition of Acanthamoeba–Induced Cytopathic Effect," Molecular Parasitology Meeting VIII, Woods Hole, Massachusetts, Abstract Book, p. 422, Sep. 24–28, 1997.

Panjwani, N. et al., "Acanthamoeba Bind to Rabbit Corneal Epithelium In Vitro," *Investigative Opthalmology & Visual Science* 38(9):1858–1864, 1997.

Yang, Z. et al., "Pathogenesis of Acanthamoeba Keratitis: Carbohydrate–Mediated Host–Parasite Interactions," *Infection and Immunity* 65(2):439–445, Feb. 1997.

*Primary Examiner*—Kathleen K. Fonda
*Attorney, Agent, or Firm*—Clark & Elbing LLP

[57] ABSTRACT

Microbe-inhibiting compositions including N-acetylglucosamine and methods of using them.

2 Claims, No Drawings

MICROBE-INHIBITING COMPOSITIONS

STATEMENT AS TO FEDERALLY SPONSORED RESEARCH

Research relating to some of the subject matter disclosed herein was sponsored by grants EY09349 and EY07088 from the National Eye Institute. As a result, the Federal Government may have rights in some portion of the disclosed inventions.

BACKGROUND OF THE INVENTION

The invention relates to compositions which inhibit microbial infection. Microbes include parasites such as *Acanthamoeba castellanii, A. culbertsoni, A. hatchetti, A. polyphagia, A. rhysodes, Entamoeba histolytica, Giardia lamblia, Leishmania amazomen,* and *Trypanosoma cruzi*; and bacteria such as *Pseudomonas aeruginosa*. Acanthamoeba are present in soil, air, swimming pools, hot tubs, tap water, and contact-lens care products. Individuals who are susceptible to opportunistic pathogens such as Acanthamoeba include those who are chronically ill, immunocompromised, pregnant, diabetic, or suffer from liver disease or alcoholism. Immunocompromised individuals include patients with lymphoma, leukemia, or AIDS, and those taking immuno-suppressive medication such as organ transplant patients. Acanthamoeba infections include granulomatous amebic encephalitis and cutaneous lesions. In immunocompetent individuals, Acanthamoeba cause a vision-threatening corneal infection known as Acanthamoeba keratitis. Many patients with Acanthamoeba keratitis are contact lens wearers. Current therapy includes the use of Brolene and neomycin, or clotrimazole.

SUMMARY OF THE INVENTION

The invention features a method for inhibiting an infection of a microorganism. The method includes administering to a patient a composition including a pharmaceutically effective amount of N-acetylglucosamine. For example, the microorganism can be a parasite selected from species of Acanthamoeba and Pseudomonas. Preferably, the microorganism is a bacteria or parasite known to secrete proteinase as part of its pathogenic mechanism. Species of Acanthamoeba include *A. castellanii, A. polyphagia, A. culbertsoni, A. hatchetti,* and *A. rhysodes*. Species of Pseudomonas include *P. aeruginosa* and *P. capecia*. An Acanthamoeba infection can be an infection of the skin, the brain, or the eye, such as the cornea. A Pseudomonas infection can be an infection of the eye or the lungs. In one preferred aspect, the infection is not coccidiosis.

The invention also features a composition that includes N-acetylglucosamine, or includes N-acetylglucosamine and methyl-α-mannopyranoside. This composition is useful in inhibiting a microbial infection, such as parasitic infection, or an Acanthamoeba or Pseudomonas infection. The disclosed compositions generally contain at least 0.05% N-acetylglucosamine by weight and, in some embodiments, at least 0.05% methyl-α-mannopyranoside by weight.

A composition of the invention can be formulated for topical administration, depending on the nature and location of the infection. For example, ocular or cutaneous infections may be treated with aqueous drops, a mist, an emulsion, or a cream. Administration may be therapeutic, namely, to treat a known or suspected infection, or it may be prophylactic, to prevent infection. Prophylactic formulations may be present or applied to the site of potential infection, or to sources of infection, such as contact lenses, contact lens cleaning and rinsing solutions, containers for contact lens storage or transport, devices for contact lens handling, and cosmetics for the eye area, including creams, lotions, mascara, eyeliner, and eyeshadow. The invention includes ophthalmological devices or products which contain disclosed compositions, and methods of making or using such devices or products. These devices may be coated with, impregnated with, bonded to or otherwise treated with a disclosed compound or composition.

The invention also features a method for inhibiting microbial proteinase secretion. The method includes exposing a microbe to an effective amount of a composition including N-acetylglucosamine alone or including N-acetylglucosamine and methyl-α-mannopyranoside. N-Acetylglucosamine exposure may be before, during, or after the exposure to methyl-α-mannopyranoside. The two compounds, or pro-drugs thereof, may be co-administered.

DESCRIPTION OF THE PREFERRED EMBODIMENTS

The invention features a composition including N-acetyl glucosamine useful for inhibiting an infection of a microorganism such as a species of Acanthamoeba or a species of Pseudomonas, such as *P. aeruginosa* or *P. capecia*. Disclosed compositions contain at least 0.05% of N-acetylglucosamine by weight, such as 0.1%–10%, 0.2%–7.0%, or 1%–5.0%, by weight.

Inhibition of an infection of a microorganism includes (a) killing the microorganism (microcidal), (b) arresting development or reproduction of the microorganism, (c) rendering it a virulent, for example, by reducing the secretion of proteinases or other events in the pathogenic mechanism, (d) inhibiting the adhesion of the pathogen to a host cell, and (e) combinations of (a), (b), (c), and (d). Inhibition can be measured by several methods known to those in the art or described herein.

The invention includes the discovery that N-acetylglucosamine inhibits Acanthamoeba-induced host cell damage, even after the amoeba have adhered to host cells. N-acetylglucosamine may also be effective after the amoeba have penetrated the corneal stroma. The inhibition includes reducing the secretion of cytotoxic proteinases by Acanthamoeba. One aspect of the invention also includes the combined use of N-acetylglucosamine and methyl-α-mannopyranoside, the latter of which has been discovered to inhibit adhesion of Acanthamoeba to corneal surface cells.

The invention is based, in part, on the following experimental observations. The amoebic lectin has the highest affinity for α-Man, among the monosaccharides tested. The inhibitory potency of D-mannose was 10-fold less than that of α-Man. The epimers of D-mannose, altrose (C-3) and talose (C-4) were not inhibitory, and glucose (C-2) was a weak inhibitor. The configuration of free hydroxyl groups at C-2, C-3 and C-4 positions of D-mannose contribute to binding interactions. The lack of inhibitory activity in D-lyxose suggests that the $CH_2OH$ (hydroxymethyl) substituent contributes to binding. The inhibitory strengths of both mannobioses, the mannotriose and the mannopentose suggest that Man(α1-3)Man disaccharide, which is three times more potent than the corresponding α-1-6 disaccharide, is the most complementary to the carbohydrate-binding site of the amoebic lectin. Elongation of the Man (α1-3) chains with additional mannose units only slightly increased affinity.

The carbohydrate-binding properties of the amoebic lectin are both distinct from and more specific than the mannose-specific animal lectins of liver, macrophage and serum. First, the affinity of mannose-specific animal lectins for α-Man is either similar to or slightly higher than for D-mannose. In contrast, regarding the amoebic lectin, the inhibitory potency of α-Man was ten times that of D-mannose and eight times that of β-Man. Unlike the other animal lectins, the amoebic lectin is sensitive to the anomeric configuration of mannose. Second, although rat liver and serum lectins have the highest affinity for N-acetylmannosamine, N-acetylmannosamine did not inhibit binding of the amoebic lectin to Man-BSA even at 100 mM. Both rat liver and serum mannose-lectins are also known to have affinity for GlcNAc and α-fucose. While these two sugars were weak inhibitors of amoebae binding to Man-BSA, amoeba did not bind to microtiter wells coated with BSA-GlcNAc or BSA-fucose. Turning to another animal lectin, alligator liver lectin has similar affinities for α-Man, D-mannose and D-lyxose. However, the amoebic lectin is distinguished among these three saccharides, having a considerably higher affinity for α-Man than D-mannose, and having no affinity for D-lyxose. In view of the above, the ligand-specificity of the amoebic lectin is narrower than most liver and serum mannose-specific lectins.

The invention relates, in part, to the discovery that intact amoebae and Acanthamoeba-conditioned media (ACM) damage the corneal monolayer (host cell) in vitro by distinct mechanisms. On the one hand, the trophozoite-induced host cell loss resulted from three sequential steps: (i) adhesion of amoeba to host cells (<1 hour), (ii) cytolysis of the host cells, demonstrated by chromium release and the presence of cell-free plaques in the monolayer which increase in size with time, and (iii) detachment of the monolayer surrounding the plaques from the culture dish (18–20 hours). On the other hand, ACM mediated a cytolysis-free cytopathic effect (CPE) which included detachment of the monolayer from the culture dish. No evidence of cytolytic processes, such as plaques, cell-free areas, or chromium release, was observed in the monolayer incubated with ACM. According to the invention, amoebic adhesion to host cells contributes to the activation of amoeba-mediated cytolytic processes.

The invention features, in part, the discovery that Acanthamoeba secrete proteinases which could be detrimental to the host cells, and that the carbohydrate-mediated adhesion of amoebae to host cells affects the proteinases produced by the parasite and/or host cells. A specific metalloproteinase (P3) was produced by the parasite only upon mannose-mediated direct contact of the parasite to target cells. In addition, contact-independent events should be considered. For example, secretion of a serine proteinase (P2) is elevated upon incubation of the amoebae with the host cells. When the amoebae adhesion to the host cells was blocked by α-Man, the amoebic proteinase P3 was not expressed, and yet P2 was robustly expressed. This suggests that P2 secretion is independent of host-amoeba contact and possibly related to a host secretory factor. The pathogenic strains of Acanthamoebae produce markedly elevated levels of phospholipases which could potentially render the host cells susceptible to attack by proteinases.

The invention is further related, in part, to the discovery that GlcNAc inhibits CPE, even though GlcNAc is a poor inhibitor of amoebic adhesion to the target cells. Addition of GlcNAc to the culture medium used to produce condition media resulted in an ACM which inhibited the CPE. Yet, addition of GlcNAc to ACM after the media was produced did not result in inhibitory media. Furthermore, removal of GlcNAc from ACM by Centricon filtration did not prevent the filtered ACM from inhibiting CPE.

In view of the above, GlcNAc inhibited the ACM-induced CPE indirectly, for example, by influencing the expression of the molecules involved in the cytopathogenic mechanisms of Acanthamoeba, such as cytotoxins, inhibitors of proteinases, or pore-forming amoebic proteins. Many transcription factors are post-translationally modified with O-linked GlcNAc monosaccharide on serine and/or threonine residues. Almost all O-GlcNAc-bearing proteins are phosphoproteins, and it has been shown that phosphorylation could occur at the same serine/threonine residues that are targeted for glycosylation. O-GlcNAc modification has a regulatory role in gene expression, possibly by controlling phosphorylation at identical or nearby sites. Exogenous GlcNAc can penetrate the interior of the cell leading to an increase in the intracellular concentration of UDP-GlcNAc, a substrate for protein glycosylation. The glycosylation of one or more sites which otherwise would have been phosphorylated could result in the loss of the function of the transcription factor.

Regardless of the mechanism, the use of GlcNAc alone or in conjunction with α-Man-based saccharides has therapeutic potential according to the invention. These saccharides are nontoxic and can be delivered topically to the eye either in the form of eye drops or from contact lenses designed to deliver small continuous doses of drugs to the eye.

EXAMPLES

Example 1

In vitro cytopathic assays were performed using cell cultures of corneal epithelium as target cells. Primary cell cultures of rabbit corneal epithelium were prepared according to published protocols (M. M. Jumblatt, *Invest. Opthalmol. Visual Sci.* 24:1139–43, 1983) using rabbit eyes from Pel-Freez Biologicals (N. Panjwani et al., *Invest. Opthalmol. Visual Sci.* 31:689–695, 1990) (Rogers, AK). Generally, seventy-five eyes were processed at a time. Primary cultures have limited life span and can only be passaged 2 to 3 times without significant alteration in cell morphology.

Corneal epithelial cells with extended life span were also produced. The epithelial origin of the transformed cells was established by a positive reaction with mAb AE5 (ICN BioMed, Inc., Aurora, Ohio) which reacts with the corneal epithelial cell marker keratin K3.

To characterize the role of carbohydrate-mediated host-parasite interactions in the Acanthamoeba-induced cytotoxicity of host cells, in vitro cytopathic assays were performed using both primary and immortalized cultures of corneal epithelium as host cells. Immortalized cells were assayed as confluent cultures in 24-well plates, and primary cells were assayed as confluent cells in 35-mm dishes or 6-well plates.

The parasites (>95% trophozoites) were rinsed three times in a serum-free Eagle's minimum essential medium supplemented with 0.4% bovine serum albumin (SFB) and aliquots of the parasite suspension ($0.2 \times 10^5$ to $1 \times 10^6$ parasites/ml SFB medium, 300 μl/well for 24-well plates and 500 μl/well for 6-well plates or 35-mm dishes) were added to wells of confluent epithelial cultures which had been rinsed and preincubated in SFB medium for 2 hours. The plates were incubated at 37° C. in a $CO_2$ incubator and periodically examined under a phase-contrast microscope for the presence of cell-free plaques in the monolayer for up to 28–30 hours. Control wells contained host cells without the parasites. At the end of the incubation period, the cultures were stained with Giemsa (Diff-Quik, Dade Diagnostic Inc., Aguada, PR). Approximate cell density in each well was estimated by scanning the stained plates in a calibrated, computer-assisted Bio-Image Scanner (Millipore, Ann Arbor, Mich.). Cytopathic effect (CPE) was expressed as percentage of the optical density by the following formula:

$$\% \text{ CPE} = \frac{\text{O.D. of epithelial cells incubated with amoeba}}{\text{O.D. of control cells}} \times 100$$

Acanthamoeba trophozoites have been shown to produce a CPE on a variety of cultured mammalian cells.

To determine whether the carbohydrate-mediated adhesion of Acanthamoeba to corneal epithelium is a prerequisite for the parasite-induced host cell damage, the CPE assays were performed in the presence and absence of various saccharides. The pathogenic ocular isolate of Acanthamoeba used in the present study produced extensive cytolysis of both immortalized as well as primary rabbit corneal epithelial cells in culture. During the early phase (8 hours–10 hours) cytolysis was only detected by the appearance of small cell-free plaques in the monolayers. With the continued incubation with the amoebae, the size of the cell-free areas increased, and eventually the monolayer surrounding the large plaques lifted entirely from the culture dish resulting in almost complete loss of the cell layer.

In short, in the early phase, amoebae-induced target cell loss was due to cytolysis. The CPE, i.e., the detachment of the cells from the culture dish, was detected only after prolonged incubation. The extent of monolayer destruction depended on the concentration of amoebae, the nature of cell cultures (primary vs. immortalized), the length of the incubation period, and media composition. When immortalized cultures were used, an amoebic concentration of $2 \times 10^5$ cells/ml was required to completely destroy the monolayer within 24 hours. All CPE assays were performed in a serum-free medium supplemented with 0–0.4% BSA (SFB). If BSA was omitted from the media, the destruction of the monolayer occurred approximately twice as fast.

Example 2

A variety of sugars (0.03 to 100 mM) were tested for inhibitory activity against amoeba-induced CPE using immortalized cell cultures (see Table 1). The effect of some saccharides on Acanthamoeba-induced CPE on primary cultures of corneal epithelium was also determined (see Table 1). Not shown in Table 1 are several sugars which, at 100 mM, did not inhibit Acanthamoeba binding to Man-BSA or the amoeba-induced cytopathic effect. These were L-mannose, D-mannitol, N-acetyl-D-mannosamine, D-mannose-6-phosphate, D-altrose, D-lyxose, α-D-talose, methyl-β-D-glucopyranoside, methyl-α-D-galactopyranoside, methyl-β-D-galactopyranoside, N-acetyl-D-galactosamine and L-rhamnose. D-glucosamine and D-mannosamine also did not inhibit the amoeba binding to Man-BSA at 100 mM. Toxic to the epithelium upon overnight incubation, these two sugars were not analyzed for either inhibition of cytolysis or CPE.

TABLE 1

Inhibition by Saccharides on Acanthamoeba binding to Man-BSA and Acanthamoeba-induced Cytopathic effect

| Saccharide | Inhibition of binding to Man-BSA (conc. in mM for 50% inhib.) | Inhibition of cytopathic effect (% inhib. at indicated conc.) |
| --- | --- | --- |
| D-mannose | 20 | 50% at 5mM |
| Methyl-β-D-mannopyranoside | 16 | N.D. |
| Man(α1-6)Man | 2.4 | 80% at 0.31 mM |
| Methyl-α-D-mannopyranoside | 1.96 | 61% at 0.31 mM |
| Man(α1-3)Man | 0.74 | 91% at 0.31 mM |
| Man(α1-3)Man(α1-6)Man | 0.62 | 100% at 0.31 mM |
| Man(α1-3)Man(α1-6)Man(α1-3)Man(α1-6)Man | 0.44 | N.D. |
| D-mannose-6-phosphate | No inhibition at 100 mM | 30% at 50 mM |
| Methyl-α-D-glucopyranoside | 40% at 100 mM | 31% at 50 mM |
| N-acetyl-D-glucosamine | 50% at 50 mM | 60% at 0.31 mM |
| α-L-Fucose | 28 mM | 40% at 100 mM |

The CPE assays were performed in the SFB media containing one or more saccharides to be tested. The relative inhibitory potency of each saccharide was estimated by terminating the CPE assays when the culture wells incubated with amoeba in the absence of saccharides exhibited approximately 50% destruction of the monolayer by phase-contrast microscopy (10 hours–14 hours). After staining with Giemsa, percent cell loss in each well was calculated based on the optical density in each well. A direct correlation between the ability of the sugar to inhibit the Acanthamoeba binding to Man-BSA and to inhibit the amoeba-induced CPE was found, with one notable exception, GlcNAc (Table 1). Methyl-α-mannopyranoside, both mannobioses, the mannotriose and the mannopentose which were potent inhibitors of amoebic binding to Man-BSA were also potent inhibitors of amoeba-induced CPE. Saccharides which did not inhibit amoebic binding to Man-BSA also did not inhibit the amoeba-induced CPE. Examples in this group include mannitol, mannosamine, methyl α- and methyl β-galactopyranoside, and N-acetyl-D-mannosamine. Similarly, methyl α-D-glucopyranoside and α-L-fucose were poor inhibitors of both Acanthamoeba binding to Man-BSA and the amoeba-induced CPE. An exception to this apparent correlation was GlcNAc, a weak inhibitor of the amoebic adhesion and yet a potent inhibitor of amoeba-induced CPE as discussed in the next section.

Primary cultures were less susceptible to amoeba-induced CPE, requiring $1 \times 10^6$ parasites/ml to completely destroy the monolayer within 24 hours. This parasite concentration was five times higher than that required to produce the same effect when immortalized cultures were used as target host cells. Only a limited number of saccharides were tested for their ability to inhibit the amoeba-induced destruction of primary cultures. α-Man, both mannobioses, the mannotriose and the mannopentose inhibited CPE; GlcNAc also inhibited both CPE. Methyl-α-D-galactopyranoside and methyl-β-D-galactopyranoside did not inhibit CPE. α-L-fucose, a weak inhibitor of both Acanthamoeba binding to Man-BSA and the amoeba-induced CPE of immortalized cultures, was not inhibitory when primary cultures were used as target cells.

The inhibitory potency of GlcNAc in the amoeba adhesion assay was 26 times less than that of α-Man. In contrast, in the CPE assays, the inhibitory potencies of both α-Man and GlcNAc were nearly identical. When amoebae were incubated with monolayers, amoeba adhered to the monolayer cultures within minutes. In the presence of α-Man, amoebae did not adhere to the cell monolayer and amoeba-induced cytolysis of the corneal epithelial cells was substantially inhibited. Cell-free plaques were not detected in the presence of α-Man.

In the absence of α-Man, nearly complete loss of cell layer occurred after about 20 hours of incubation with amoebae. In the presence of α-Man, the cell layer began to lift from the periphery after about 20–28 hours incubation with the amoebae. The cell layer continued to roll inwards until the entire cell substratum layer was lifted from the dish. This occurred several hours after the complete loss of the cell layer had occurred in the cultures incubated without α-Man.

In contrast, when GlcNAc was present in the media, amoebae adhered tightly to the monolayer. Yet little evidence of cytolysis was observed. Moreover, the cell layer remained firmly adhered to the culture dish in both primary and immortalized cultures during the entire assay period of 28 hours. Since the CPE assays were performed in the serum-free media, incubations were not continued beyond 28 hours. This demonstrated that α-Man and GlcNAc modulate Acanthamoeba-induced CPE by distinct mechanisms.

Example 3

To determine whether the mechanism modulating the CPE produced by intact amoeba and amoeba-conditioned medium (ACM) are distinct, CPE and assays were also performed using ACM in the presence and the absence of saccharides. To produce ACM, exponentially growing parasites (>95% trophozoites) in PYG media (Proteose Peptone-yeast extract-glucose , J. T. Bornes et al., J. Parasitol. 56:904–906, 1970) were rinsed twice with SFB medium and incubated in serum-free SFB medium at concentrations between $2 \times 10^5$ to $1 \times 10^6$ cells/ml in a $CO_2$ incubator for 24 hours. After removing the parasites by centrifugation, each supernatant was analyzed for its ability to induce CPE. Saccharides (α-Man and GlcNAc, 50 mM) were added either to the ACM after it was produced or to serum-free medium used to produce an ACM. The ACM produced in the presence of the saccharides was also analyzed after removal of the saccharides by centrifugation through Centricon 3 microconcentrators (Amicon Inc., Beverly, Mass.).

To determine the role of the parasitic secretory factors in the cytopathogenic mechanism, chromium release and CPE assays were performed using ACM. In this study, parasites were incubated in the SFB media for 24 hours, centrifuged to remove parasites and the conditioned medium was tested for its ability to produce cytolysis and CPE. The ACM produced remarkable CPE. However, based on the chromium release data and the absence of cell-free plaques in the monolayer, no cytolysis was observed in the cultures incubated with ACM. Approximately 6 to 8 hours following the incubation of the monolayer with the ACM, the cell sheet at the edges of the monolayer began to lift and roll inwards and eventually the entire monolayer lifted en bloc from the dish. These observations were similar to those seen when the monolayers were incubated with trophozoites in the presence of α-Man. Unlike the CPE induced by intact amoeba, the CPE induced by the ACM was not inhibited by either α-Man or GlcNAc when the sugars were added to the ACM after it was produced. In the next set of experiments, ACM was produced in the presence of α-Man or GlcNAc and was tested for CPE-inducing activity. The ACM produced in the SFB alone or in the SFB containing α-Man strongly induced CPE. In contrast, the ACM produced in the SFB containing GlcNAc did not induce CPE. In addition, the filtrate and retentate obtained after filtering the ACM in Centricon 3 microconcentrators were tested for CPE-inducing activity. When the ACM was produced in the absence of either sugar, substantially all of the CPE-inducing activity was found in the retentate obtained after Centricon filtration. However, the ACM produced in the presence of GlcNAc did not have CPE-inducing activity even after removal of GlcNAc by filtration.

Example 4

To characterize the mechanism by which the mannose-mediated host-parasite interactions influence the amoeba-induced cytolysis and/or cytopathic effect, conditioned media obtained by incubating amoebae with primary cultures of corneal epithelium in the presence and absence of α-Man for 6 to 8 hours were analyzed by zymography. Media conditioned by only Acanthamoeba or only epithelial cells were also analyzed. Zymography was performed using separating gels containing 10% acrylamide and 2 mg/ml gelatin, essentially as described by D. E. Kleiner et al. (*Anal Biochem.* 218:325–329, 1994). Samples were diluted in the electrophoresis sample buffer (U. K. Laemmli, *Nature* 227:680–685, 1970) without mercaptoethanol and were applied to the gels. After electrophoresis, proteinases separated on the gels were renatured by incubating the gels in 2.5% Triton X-100 in 50 mM Tris-HCl, pH 7.5 to remove SDS. After incubating the gels for 18 hours in a developing buffer (50 mM Tris-HCl, pH 7.5 containing 10 mM $CaCl_2$), the gels were stained with Coomassie brilliant blue. Areas of digestion were visualized as non-staining regions. In some experiments, samples were pre-treated with phenylmethyl-sulfonyl fluoride (PMSF, 1 mM), an inhibitor of serum proteinases for one hour prior to electrophoresis, or 1,10-phenanthroline (1 mM), an inhibitor of metalloproteinases, was added to the developing buffer.

In these experiments, four components (P1, 230 kD; P2, 97 kD; P3, 80 kD; and P4, 55 kD; average values from four gels) were detected in the samples obtained after incubating amoebae with primary cultures of corneal epithelium in media alone for 6 hours. When adhesion of amoebae to the host cells was inhibited with α-Man, P3 was not detected. In other words, P3 expression was dependent on the mannose-mediated adhesion of amoeba to host cells. In the ACM media prepared by incubating parasites in the media alone, or in the media containing a-Man, mainly components P1 and P4 with trace amounts of component P2 were seen. Components P1, P2 and P4 were susceptible to PMSF, but were resistant to 1,10-phenanthroline. In contrast, component P3 was susceptible to 1,10-phenanthroline and resistant to PMSF. In the media conditioned by epithelial cells alone, two components (E1, 93 kD; E2, 63 kD; average values of two gels) were seen, both of which were found to be resistant to PMSF and susceptible to 1,10-phenanthroline. This demonstrated that carbohydrate-mediated adhesion of Acanthamoebae to host cells induces expression of a metalloproteinase, P3.

Example 5

The Acanthamoeba strain MEEI 0184 (A. castellani based on morphological characteristics) was derived from an infected human cornea and used throughout this study. ATCC strain 30868 should have similar properties. The parasites were axenically cultured in PYG medium. A solid-phase assay characterized the sugar binding properties of the mannose binding protein (MBP) of Acanthamoeba (Z. Yang et al., *Infect. Immun.* 65:439–445, 1997). Briefly, wells of microtiter plates were coated with bovine serum albumin-α-D-mannopyranosyl phenylisothiocyanate (Man-BSA, 15–25 moles of α-D-mannopyranoside/mole albumin, 0.03 µg/ml, 50µl/well in 0.1 M sodium carbonate buffer, pH 9.6, 4° C. overnight). Nonspecific binding was blocked with 1% BSA in phosphate buffered saline (PBS, 1 hour, room temperature). After adding a 50-µl aliquot of $^{35}$S-labeled Acanthamoeba ($5 \times 10^6$ cells/ml in PBS; 1 to 2 cpm/parasite, >95% trophozoites) to each well, the plates were incubated for 2 hours at room temperature. After rinsing the cells with PBS to remove unbound Acanthamoeba, 0.1 ml of 2% sodium dodecyl sulfate (SDS) was added to each well, and the radioactivity in aliquots of solubilized material was determined in a scintillation counter. The data demonstrated Acanthamoeba bind α-Man and α1-3-linked mannose residues with the highest affinity.

Example 6

To determine whether any other lectin, besides the amoebic mannose binding protein (MBP), is present on the amoeba surface, solid-phase assays were performed using microtiter wells coated with a number of neoglycoproteins including N-acetyl-D-glucosamine-BSA(GlcNAc-BSA), N-acetyl-galactosamine-BSA, fucose-BSA and galactose-BSA (Sigma). These neoglycoproteins contained 15–30 moles sugar/mole albumin. The data showed amoebic mannose-specific lectin is most likely the only carbohydrate-binding protein present on the Acanthamoeba plasma membrane.

Example 7

Chromium release experiments were performed to confirm the absence or occurrence of cytolysis. Visually, cell plaques or bare spots in a culture can indicate either cell loss by cytolysis, or separation of the cell from the culture surface, wherein detached cells, although initially viable, subsequently die. Cell lysis was quantified by measuring $^{51}$Cr release from prelabeled cells. After incubating confluent monolayer cultures of corneal epithelium in 24-well plates in cell culture medium containing Na$^{51}$CrO$_4$ (460 mCi/mg, 12 μCi/ml) for 18–20 hours, the cells were thoroughly rinsed and incubated with Acanthamoeba (1×10$^6$ parasites/ml SFB media). The four groups were (i) Acanthamoeba in media alone, (ii) Acanthamoeba in media containing α-Man, (iii) Acanthamoeba in media containing GlcNAc, and (iv) Acanthamoeba condition media. When approximately 50–70% cell loss occurred based on phase contrast microscopy, aliquots of cell-free conditioned medium from each well were analyzed. Supernatants from the four wells in each group were pooled before analysis. Percent specific release was calculated using E/T×100, where E is CPM released in test well minus CPM released in control (parasite-free) well and T is the total CPM (CPM cells+CPM supernatant in control wells). "CPM cells" was determined by incubating control wells with 0.5% Triton X-100. Conditioned media from each well was also analyzed for lactate dehydrogenase (LDH) release using an LDH assay kit (Sigma).

The $^{51}$Cr data showed that Acanthamoeba mediate cytolysis, although the extent of cytolysis did not correlate with the extent of CPE. The percentage specific release for the above-described groups (i)–(iv) were, respectively, about 100, 28, 80, and 13. When approximately 50% cell loss had occurred in CPE assays, the percent specific $^{51}$Cr release was about 12.5%. Fifty millimolar α-Man inhibited more than 70% of amoeba-induced cytolysis. In contrast, GlcNAc is a weak inhibitor at the same concentration, with inhibition values of 10–20%. Similar results were found using LDH release assays. $^{51}$Cr release assays also showed that ACM did not induce cytolysis (see Example 3).

Other Embodiments

From the disclosure herein, the essential features of the invention will be readily apparent to one of ordinary skill who, without undue experimentation, will be able to modify or adapt the invention to various uses or conditions without departing from the spirit and scope of the claims. Publications cited herein, although generally provided for the reader's convenience to describe methods well known in the art, are hereby incorporated by reference in their entirety.

What is claimed is:

1. A method for inhibiting an infection by a microorganism, said method comprising administering to a patient a composition comprising a pharmaceutically effective amount of N-acetylglucosamine, wherein said microorganism is selected from the group consisting of *A. castellanii, A. polyphagia, A. culberstoni, A. hatchetti*, and *A. physodes.*

2. A method of inhibiting an Acanthamoeba infection of a cornea of a patient wherein a characteristic of said infection is secretion of proteases, said method comprising administering to said patient a pharmaceutically effective amount of N-acetylglucosamine.

* * * * *